(12) United States Patent
Dai (10) Patent No.: US 11,642,546 B2
(45) Date of Patent: May 9, 2023

(54) LED FACIAL MASK

(71) Applicant: Shanghai Edge Light Industry Co., Ltd., Shanghai (CN)

(72) Inventor: Wenhui Dai, Shanghai (CN)

(73) Assignee: Shanghai Edge Light Industry CO., LTD, Shanghai (CN)

( * ) Notice: Subject to any disclaimer, the term of this patent is extended or adjusted under 35 U.S.C. 154(b) by 0 days.

(21) Appl. No.: 15/538,596

(22) PCT Filed: Dec. 29, 2014

(86) PCT No.: PCT/CN2014/001189
§ 371 (c)(1),
(2) Date: Mar. 10, 2022

(87) PCT Pub. No.: WO2015/135098
PCT Pub. Date: Sep. 17, 2015

(65) Prior Publication Data
US 2019/0015680 A1    Jan. 17, 2019

(30) Foreign Application Priority Data

Mar. 10, 2014    (CN) .................... 2014 2 0105675 U (51) Int. Cl.
    *A61N 5/06*      (2006.01)
    *H05K 1/18*      (2006.01)
    *A61B 18/00*    (2006.01)

(52) U.S. Cl.
CPC .......... *A61N 5/0616* (2013.01); *H05K 1/189* (2013.01); *A61B 2018/00452* (2013.01); *A61N 2005/0647* (2013.01); *A61N 2005/0652* (2013.01)

(58) Field of Classification Search
CPC .. A61N 5/0616; A61N 5/0647; A61N 5/0652; A61N 5/0663; A61N 5/06;
(Continued)

(56) References Cited

U.S. PATENT DOCUMENTS 9,724,536 B1 * 8/2017 Rabin ................... A61N 5/0617
2003/0202338 A1 * 10/2003 Parker ................... A61M 21/02
362/602
(Continued)

FOREIGN PATENT DOCUMENTS

CN          2899842 Y  *  5/2007
CN   200580039038      1/2008
(Continued)

OTHER PUBLICATIONS

International Search Report (English Translation) for PCT/CN2014/001189 dated Sep. 17, 2015.
(Continued)

*Primary Examiner* — Rex R Holmes
*Assistant Examiner* — Sana Sahand
(74) *Attorney, Agent, or Firm* — Crawford Intellectual Property Law LLC; Brie A. Crawford (57) ABSTRACT

An LED facial mask incorporates a transparent light guide which distributes therapeutically useful frequencies of light over the skin of a user's face. Further, a USB connection port provides power. Alternate embodiments incorporate the mask device into alternate forms of wearable devices.

3 Claims, 4 Drawing Sheets

(58) Field of Classification Search
CPC .... A61N 2005/0652; A61N 2005/0653; A61N 2005/0645; A61N 2005/0647; A61B 18/00452
See application file for complete search history.

(56) References Cited

U.S. PATENT DOCUMENTS

| | | | | |
|---|---|---|---|---|
| 2010/0076529 | A1* | 3/2010 | Tucker | A61N 5/0616 607/90 |
| 2011/0104633 | A1* | 5/2011 | Levine | A61C 19/063 433/29 |
| 2012/0139445 | A1* | 6/2012 | Fujiwara | G02F 1/133603 315/294 |
| 2012/0323064 | A1* | 12/2012 | Kim | A61K 9/0048 600/15 |
| 2013/0066404 | A1* | 3/2013 | Tapper | A61F 9/045 607/90 |
| 2013/0190845 | A1* | 7/2013 | Liu | A61N 5/0616 607/90 |
| 2014/0379053 | A1* | 12/2014 | Boo | A61N 5/0616 607/89 |

FOREIGN PATENT DOCUMENTS

| | | | | |
|---|---|---|---|---|
| CN | 201110230056 | | 1/2012 | |
| CN | 201210392410 | | 1/2013 | |
| CN | 201320324090 | | 11/2013 | |
| CN | 103785114 A | | 5/2014 | |
| CN | 203677744 U | | 7/2014 | |
| CN | 203750027 U | | 8/2014 | |
| CN | 203777510 U | | 8/2014 | |
| CN | 203944028 U | | 11/2014 | |
| CN | 203944029 U | | 11/2014 | |
| CN | 204033811 U | | 12/2014 | |
| CN | 103861214 B | | 4/2016 | |
| KR | 20110117481 A | * | 4/2010 | .......... A61N 5/0616 |
| KR | 20120063169 A | * | 12/2010 | ............ A45D 44/22 |
| KR | 20110100122 A | * | 9/2011 | |
| KR | 101350503 B1 | * | 1/2014 | .......... A45D 44/002 |
| KR | 3008096790000 | | 8/2015 | |
| WO | 2013036558 A1 | | 3/2013 | |

OTHER PUBLICATIONS

Written Opinion of the International Searching Authority (English Translation) or PCT/CN2014/001189 dated Apr. 1, 2015.

* cited by examiner

LED FACIAL MASK

This invention relates to an LED facial mask incorporating a transparent light guide which distributes therapeutically useful frequencies of light over the skin of a user's face safely and conveniently.

PRIORITY CLAIM

This application claims priority from one or more previously filed foreign or PCT applications, namely:
A New Type of LED Facial Mask, WO2015135098 A1 (PCT/CN2014/001189).

BACKGROUND OF THE INVENTION

Optics has long been applied in medical care. Phototherapy has been an ancient method for treating human diseases. As early as thousands of years ago, countries like China and Egypt were already using sunlight to treat diseases.

The invention of the laser in 1960 marked a new age for phototherapy. The high luminance, monochromaticity, and wavelength selectivity of lasers has contributed to their huge success in ophthalmological, dermatological, and surgical applications. For a long time, however, the high cost of laser devices has been an obstacle for the development and widespread use of medical lasers. A device which could administer phototherapy without the need for a laser emitter to provide the photoradiation would be a useful invention.

Light emitting diode (LED) technology has been on the rise as a less expensive means of providing phototherapy. The advantages of LED, such as high density, multiple wavelengths, long lifespan, and small size, have laid a solid foundation for the application of LED in medical care and for its partial replacement of laser devices. Compared with lasers, LED has lower cost, lower energy consumption, and higher stability, which makes them suitable for a wider range of applications in medical care. A device which provides phototherapy with LED emitters would be a useful invention.

In particular, specific frequencies of light have been shown in a variety of circumstances to have particular health benefits. A device which provides phototherapy with specific and selected wavelengths of light would be a useful invention.

While phototherapy products are known in the art, generally all currently used technologies have one or more of the following deficiencies:
1. They use illumination by conventional direct irradiation which can irritate the skin and which requires large sources of illumination to effectively irradiate the entire area to be treated.
2. They use a non-transparent material (such as non-woven fabrics) as part of the distribution system and the skin is so close to the mask that it is easily irritated and/or the light source is of the proper intensity only in certain areas.
3. If a mask is incorporated, the mask itself is unwieldy. It is difficult to carry out other activities while wearing such a mask. Illuminance is strong near the light source and may cause detriment to the skin. On the other hand, areas lacking the light source are completely useless.
4. The illuminated surface (i.e. the area(s) of skin to be irradiated) has to be fixed in place, so the user cannot move freely.

A phototherapy device which did not suffer from these deficiencies would be a useful invention.

The present invention addresses these concerns.

SUMMARY OF THE INVENTION

Among the many objectives of the present invention is the provision of a device which applies phototherapy to the face.

Another objective of the present invention is the provision of a device which applies phototherapy to the face in a convenient and portable fashion.

Yet another objective of the present invention is the provision of a device which applies phototherapy to the face and allows a variety of user-controlled inputs for applying the phototherapy.

DESCRIPTION OF THE PREFERRED EMBODIMENTS

Reference will now be made in detail to several embodiments of the invention that are illustrated in accompanying drawings. Whenever possible, the same or similar reference numerals are used in the drawings and the description to refer to the same or like parts or steps. The drawings are in simplified form and are not to precise scale. For purposes of convenience and clarity only, directional terms such as top, bottom, left, right, up, down, over, above, below, beneath, rear, and front, may be used with respect to the drawings. These and similar directional terms are not to be construed to limit the scope of the invention in any manner. The words attach, connect, couple, and similar terms with their inflectional morphemes do not necessarily denote direct or intermediate connections, but may also include connections through mediate elements or devices.

The general components, and the purposes thereof, of the invention will now be described.

LED light has multiple wavelengths, among which the red light (630 nm) provides a wide variety of therapeutic effects because the mitochondria inside human tissues can absorb the resonance and introduce the absorbed photons into the body. It is also pointed out in literature that irradiation by low-energy single-wavelength red light can stimulate and promote the proliferation of fibroblasts and the synthesis of collagen.

Blue light (470 nm) can suppress acne by irradiating and eliminating *Propionibacterium acnes*, which are the main reason for inflammatory infections. This is because during metabolism, *Propionibacterium acnes* can create porphyrin, a substance that absorbs and binds with blue light of a certain wavelength and thus causes the bacteria to die.

Yellow light (590 nm) is a warm-colored, high-purity light which matches the light absorption peak of the blood vessels and thus stimulates both the lymphatic system and the nervous system.

A phototherapy device may include LED of all three types, which may be selectively activated or de-activated as the device is used, to allow selection of the most applicable type of phototherapy while conserving power and/or minimizing possible irritation by not activating LED whose emissions are not desired at the time of any particular application of phototherapy. It is required to include LED which can emit at least one of the group red, yellow or blue monochromatic lights at a wavelength reasonably known to provide phototherapeutic effect.

Phototherapy, per se, is known in the art. E.G. Chinese Patent Application Number 200580039038 "Hair Germinator", which presents a hair germinator that irradiates facial or head skin with visible light from which infrared and ultraviolet wavelengths are removed. More specifically, by using red, blue, and green light emitting diodes (LED) and controlling the supply current, the device can emit red, yellow, green, cyan, blue, and purple monochromatic lights or their combinations—in other words visible lights with wavelengths ranging from 400 to 700 nm.

Chinese Patent Application Number 201110230056.2 "LED Facial Mask Device" presents an LED facial mask device which consists of a facial mask body. LEDs are distributed on the facial mask body. The capsulation end of the LEDs is located on the inner surface of the facial mask body which fits the face. The LEDs are connected to each other with electric conductor wires. The low-level light pulses from the LEDs on the body of this LED facial mask impact the facial skin and directly act on mitochondria, thus enhancing the potential energy of the skin cells.

Chinese Patent Application Number 201210392410.6 "Variable-Shape Multi-beam Cosmetological Facial Makeup" presents a variable-shape multi-beam cosmetological facial makeup which consists of a facial makeup body. The outer surface of the facial makeup body is removably fitted to a facial makeup model. The inner surface of the facial makeup body is provided with an LED light source module. The LED light source module is composed of several LEDs of different colors which are alternately laid out. The LED light source module is electrically connected by a power cord to a controller which is used to control the light emission of the LED light source module.

Chinese Patent Application Number 201320324090.0 "LED Facial Mask" presents an LED facial mask which consists of a housing body. The housing body consists of a hard housing and a transparent hood which are fitted to each other. The clearance between the hard housing and the transparent hood contains a light emitting module, which consists of a printed circuit board and several LED lights located on the side of the printed circuit board which faces the transparent hood. A tying strap is provided at the left and right ends of the hard housing.

Having concluded the explanation of the components of the invention and the purposes thereof, and reviewed prior art, the preferred embodiment, and multiple alternate embodiments, will now be described.

Figure 1:
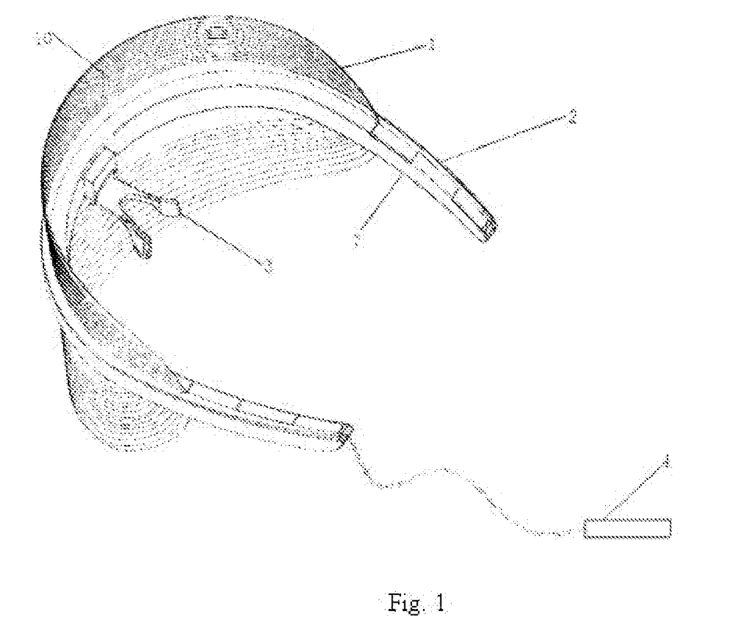
FIG. 1 depicts a perspective view of the preferred embodiment of the invention.

By referring to FIG. 1, the basic structure of a device embodying the invention may be easily understood. Device 12 consists of headpiece 2 and light guide 1 which is braced and operably captured between the headpiece 2 and retainer 7. Headpiece 2 and retainer 7 are operably attached to each other with buckles. Nosepiece 3, which is a Y-shaped nosepiece, is fixed in the middle of retainer 7. On light guide 1, there is a laser dot-dash line 10 that penetrates light guide 1. Headpiece 2 is hollow.

USB charge port 6 is provided at one end of headpiece 2. Emitter 5, comprising a flexible printed circuit LED light bar, is installed inside headpiece 2. Device 12 can also contain a battery (not shown). Emitter 5 is connected to charge port 6, through an FPC connector. If no battery is present, power source 4 must be connected to charge port 6 while the device is in operation.

Figure 5:
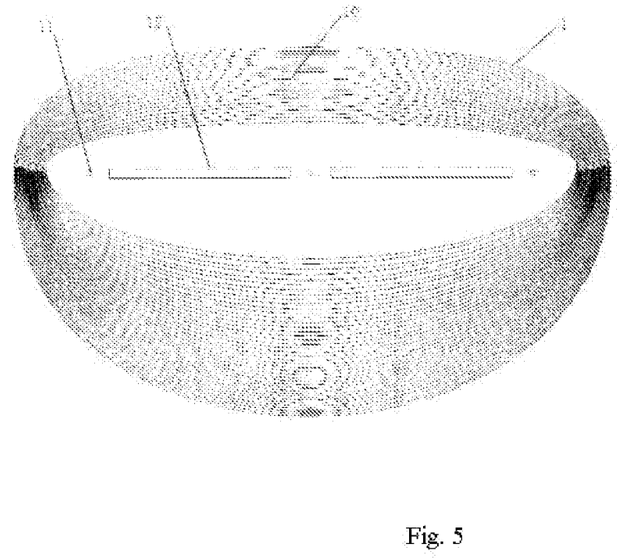
FIG. 5 depicts a frontal view of the facial mask element of the preferred embodiment.

Light guide 1 can be oval, circular, or rectangular. As shown in FIG. 5, light inputs 52, comprising two parallel rectangular holes, are opened in the middle of light guide 1. When emitter 5 is energized by the battery (not shown) and/or power source 4, light from emitter 5 passes through the light inputs 52 into the upper and lower parts of light guide 1, respectively. Light channels 51, comprising three optically open holes, are opened respectively on both ends and in the middle of light inputs 52 and correspond to positioning points on the headpiece 2. Light inputs 52 are so designed as to focus light onto the light guide 1 as much as possible and thus to increase the overall brightness of the LED facial mask. The density of dots in the dot-dash line 10 increases from the center to both ends of the line.

USB charge port 6 is a mini-USB or micro-USB charge port, as this will allow the use of standard power adapters and for device 12 to be energized by, and interface with, any appropriate device with a USB port. Charge port 6 is located on a distal end of the right side or the left side of the hollow headpiece 2.

The invention will function with emitter 5 in any reasonable operable configuration with regard to light guide 1, including at the top (see FIG. 7), the bottom, the center, or the sides.

To use the device 12, a user (not shown) dons the device by settling nosepiece 3 on their nose while headpiece 2 wraps around the upper part of the head.

Emitter 5 can be powered by any portable power bank by a USB cable, through a computer by connecting the computer to the device 12, through a USB cable, directly powered by power source 5 through USB charge port 6, solar power, or a lithium battery. Emitter 5 emits light in the wavelength(s) desired, which is transmitted into light guide 1 and refracted by dot-dash line 10 toward the user's skin, administering the desired phototherapy.

If emitter 5 comprises more than one type of LED which can emit more than one wavelength of light, there is some way to control which wavelengths (including multiple wavelengths) are emitted as the user selects the appropriate phototherapy. This could be via a switch or button.

Figure 2:
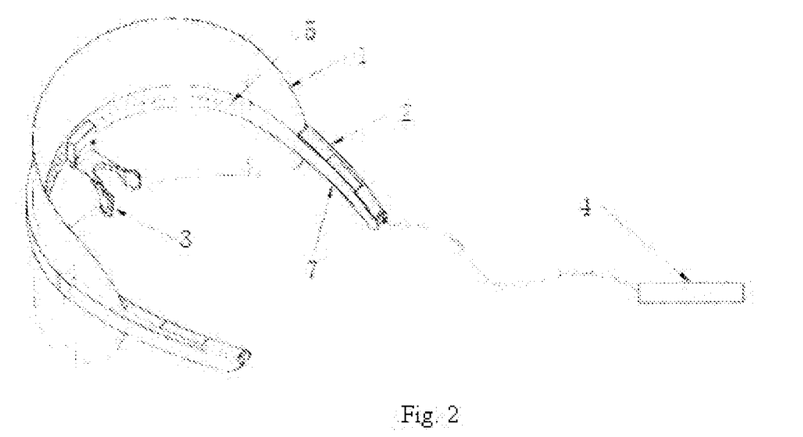
FIG. 2 depicts a perspective view of the preferred embodiment of the invention.

FIG. 2 shows the device with emitter 5, herein comprising a series of LED modules, visible through retainer 7.

Figure 3:
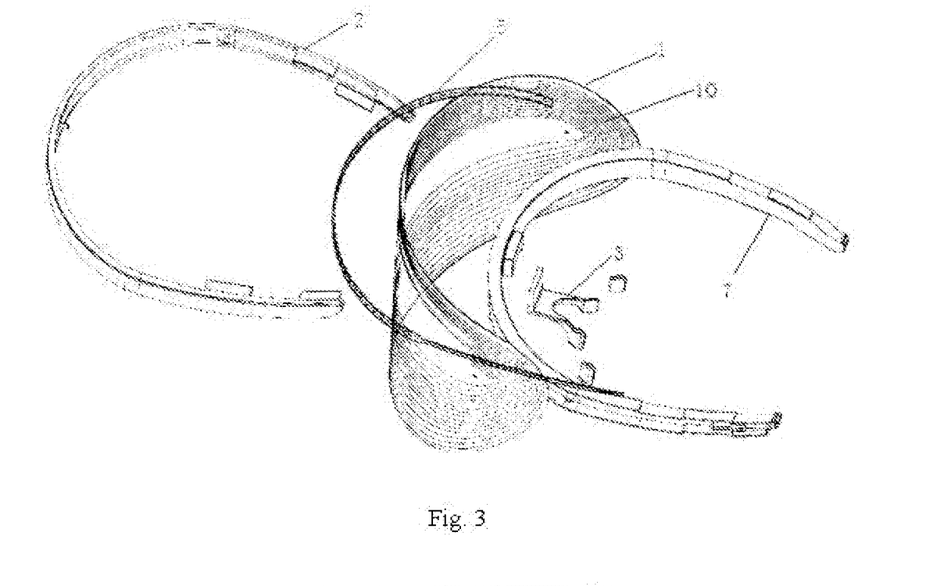
FIG. 3 depicts an exploded perspective view of the major elements of the preferred embodiment.

FIG. 3 shows the components of the device separately to better disclose the configuration of device 12. Headpiece 2 is on the outside, with emitter 5 between it and light guide 1, emitter 5 will be captured along with light guide 1 when retainer 7 is pressed into place. Nosepiece 3 will then be affixed to retainer 7 and the device will be ready for use.

Figure 4:
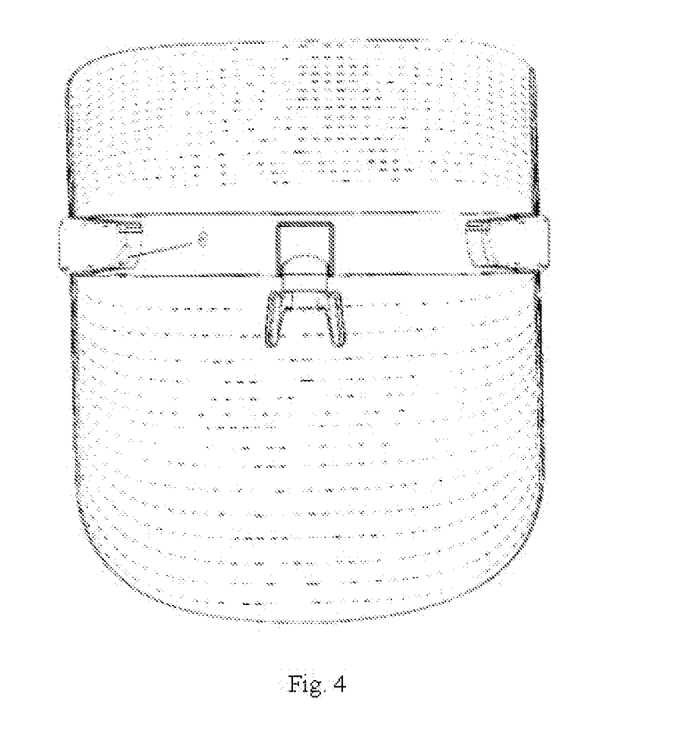
FIG. 4 depicts a rear view of the major elements of the preferred embodiment.

FIG. 4 shows the device assembled and ready for use from the perspective of someone facing the rear of device 12.

FIG. 5 shows light guide 1 from the perspective of someone facing the user (not shown.) Light inputs 52 and light channels 51 are visible and the path the light from emitter 5 can then take into light guide 1 is apparent.

Figure 6:
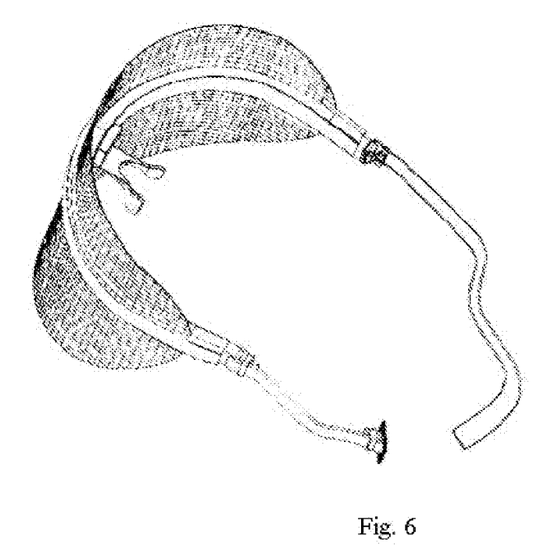
FIG. 6 depicts a perspective view of an alternate embodiment of the invention.

In FIG. 6, an improvement to the preferred embodiment comprising a strap 60 is added to the rear end of the headpiece 2 of Embodiment 1 in order to make it more comfortable to wear the device.

Figure 7:
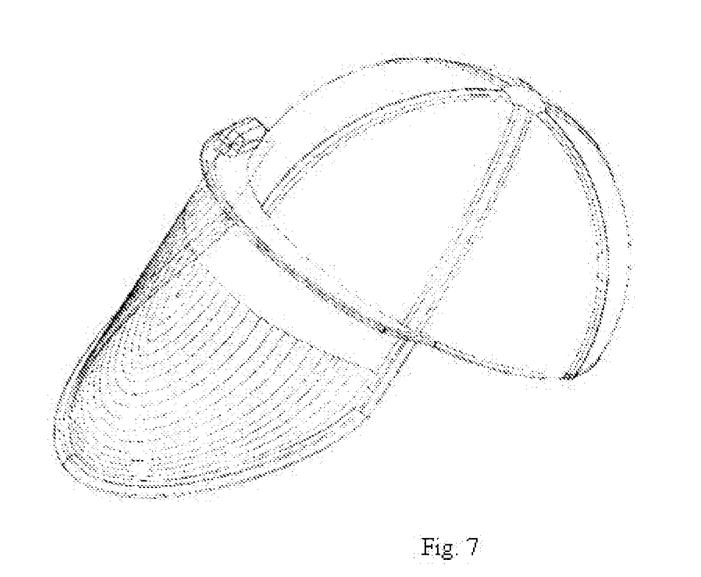
FIG. 7 depicts a perspective view of an alternate embodiment of the invention.

In FIG. 7, an alternate embodiment is shown where light guide 1 is lowered and a cap 70 is added to the top of headpiece 2 in order to make it more comfortable to wear the device and to accommodate different scenarios of use.

Figure 8:
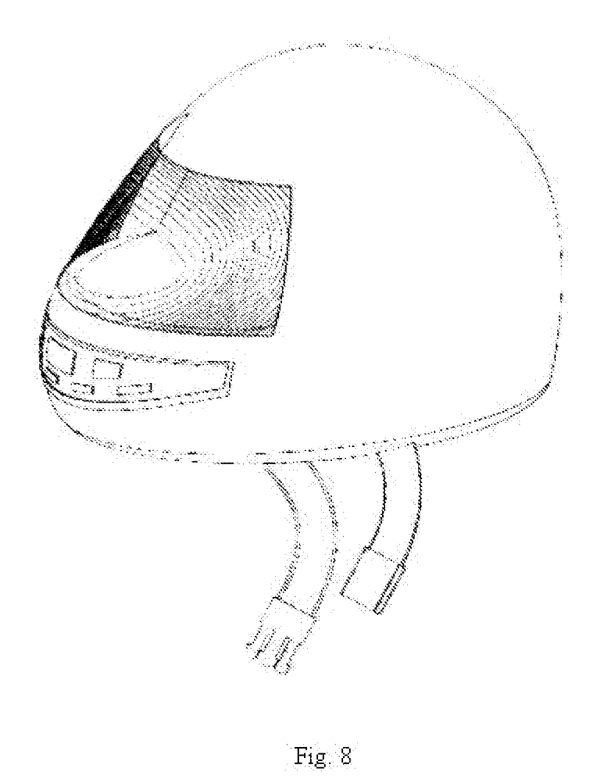
FIG. 8 depicts a perspective view of an alternate embodiment of the invention.

In FIG. 8, an alternate embodiment is shown where light guide 1 has been integrated into a helmet 80, with light guide 1 in front of the helmet 80.

Light guide 1 is made of a transparent material which transmits the light from emitter 5 to the dot-dash line 10. Light guide 1 is made of a material which will not cause any irritation or other negative effect in the majority of human beings when in proximity to or contact with the body. The dot-dash line is minimized or elminated in the area of light guide 1 opposite the user's eyes, as this reduces the amount of light directed directly into the eyes and allows the user to retain a higher level of vision.

Dot-dash line 10 can be created in light guide 1 by laser or diamond carving, screen printing, or injection molding. The actual configuration of dot-dash line 10 can include dotted lines, dashed lines, dot-dash lines, or discrete dot-dash lines. The size of the dots in dot-dash line 10 are relatively small to keep the emission of photoradiation uniform.

Injection-molding may be used to form light guide 1 and dot-dash line 10. This is done by directly making a mold of the desired shape and then molding the light guide 1 by injecting raw material. Dot-dash line 10 is injection-molded as well, so it can be directly used without having to go through further processing. This processing method saves the effort and materials of further processing of light guide 1. The body of light guide 1 may also be thicker if injection-molded without requiring hot-bending.

Light guide 1 may be oval, circular, square or irregular in shape. The thickness may range between 0.01 to 20 mm. Light guide 1 is no thicker than 20 mm. Mechanical hot bending is generally unnecessary for light guide films of 0.01 mm to 1 mm thickness, which can be directly used in device 12. Light guides 1 of 1 mm to 20 mm thickness need to be hot-bended into the desired shape as when the thickness of light guide 1 is greater than 1 mm, it is impossible to manually bend light guide 1 and attach it to headpiece 2. Therefore, mechanical hot-bending is needed.

A timing switch (not shown) is installed on the device 12. This switch may be set up as needed to achieve timed phototherapy. The timing switch can be set to a predetermined time and the device 12 will automatically power off and stop working when the predetermined amount of time has passed.

Emitter 5 is configured such that either its light emitting elements project the majority of their output along the plane of light guide 1, or that a prism or reflector be used to direct a majority of their output along the plane of light guide 1. Due to the nature of most common transparent films or plastics, some of the light from emitter 5 which enters light guide 1 will be conducted to dot-dash line 10 in almost any configuration, the configuration(s) described in this paragraph will produce the best results.

Emitter 5 can emit red monochromatic light, yellow monochromatic light, or blue monochromatic light either singularly or in combination with wavelengths ranging from 470 nanometers to 630 nanometers and emitter 5 can emit red monochromatic light with wavelengths ranging from 470 nanometers to 660 nanometers.

While various embodiments and aspects of the present invention have been described above, it should be understood that they have been presented by way of example only, and not limitation. Thus, the breadth and scope of the present invention should not be limited by any of the above exemplary embodiments.

This application—taken as a whole with the abstract, specification, and drawings being combined—provides sufficient information for a person having ordinary skill in the art to practice the invention as disclosed herein. Any measures necessary to practice this invention are well within the skill of a person having ordinary skill in this art after that person has made a careful study of this disclosure.

Because of this disclosure and solely because of this disclosure, useful modifications of this device will become clear to a person having ordinary skill in this particular art. Such modifications are clearly covered by this disclosure.

What is claimed and sought to be protected by Letters Patent is:

1. An LED facial mask comprising:
   a) the LED facial mask being attached to a hat and the hat configured to go around a head of a human user;
   b) the LED facial mask having a retainer, a headpiece, and a light guide braced between the retainer and the headpiece;
   c) an emitter which emits a visible light radiation, the emitter comprising a plurality of light emitting diodes, the emitter operably affixed to the LED facial mask;
   d) the light guide operably affixed to the LED facial mask, wherein the visible light radiation is emitted by the emitter onto the light guide and a body of the light guide is configured to transmit the visible light radiation onto a face of the human user;
   e) a dot-dash line, wherein the dot-dash line comprises at least two dots, each dot comprising a penetrating void in the light guide and the dot-dash line configured to cause a portion of the visible light radiation emitted by the emitter to be emitted onto the face of the human user;
   f) the dot-dash line having a density of dots, the density of dots increasing when the dots are closer together and the density of dots decreasing when the dots are further apart, the emitter being in a fixed position and the dot-dash line being placed, wherein there is an increase in the density of dots as the distance from the emitter becomes great over a surface of the light guide;
   g) a void in the dot-dash line, the void configured to be within a field of vision of the human user and the void configured to allow the human user to use the LED facial mask while engaging in other activities;
   h) the light guide having being 0.3 and 0.7 millimeters in thickness, wherein the thickness eliminates the need for mechanical hot bending during manufacturing;
   i) the headpiece being a hollow headpiece;
   j) the emitter being contained within the hollow headpiece;
   k) the hollow headpiece having a universal serial bus (USB) charge port;
   l) the emitter being connected to the USB charge port through an electronic connector;
   m) the emitter configured to emit a red monochromatic light, a yellow monochromatic light, or a blue monochromatic light, wherein the emitter can emit the red monochromatic light, the yellow monochromatic light, or the blue monochromatic light individually or the emitter can emit a combination of two or more of the red monochromatic light, the yellow monochromatic light, or the blue monochromatic light simultaneously;

n) the emitter being a flexible printed circuit light emitting diode (LED) light bar;
o) the light guide being made of a transparent material;
p) the electronic connector being a flat printed circuit (FPC) connector;
q) the emitter configured to emit the yellow monochromatic light or the blue monochromatic light either singularly or in combination at a wavelength between 470 nanometers to 630 nanometers and the red monochromatic light either singularly or in combination at a wavelength between 470 nanometers to 660 nanometers;
r) at least one light channel being located on the light guide, wherein the at least one light channel corresponds to a positioning point on the hollow headpiece; and
s) the USB charge port being located on a distal end of a left side or a right side of the hollow headpiece.

2. An LED facial mask comprising: a) the LED facial mask being attached to a helmet, the helmet configured to be worn by a human user; b) the LED facial mask having a retainer, a headpiece, and a light guide braced between the retainer and the headpiece; c) an emitter which emits visible light radiation, the emitter comprising a plurality of light-emitting diodes, the emitter operably affixed to the LED facial mask; d) the light guide operably affixed to the LED facial mask, wherein the visible light radiation is emitted by the emitter onto the light guide and a body of the light guide is configured to transmit the visible light radiation onto a face of the human user; e) a dot-dash line, wherein the dot-dash line comprises at least two dots, each dot comprising a penetrating void in the light guide and the dot-dash line configured to cause a portion of the visible light radiation emitted by the emitter to be emitted onto the face of the human user; f) the dot-dash line having a density of dots, the density of dots increasing when the dots are closer together and the density of dots decreasing when the dots are further apart, the emitter being in a fixed position and the dot-dash line being placed, wherein there is an increase in the density of dots as the distance from the emitter becomes greater over a surface of the light guide; g) a void in the dot-dash line, the void configured to be within a field of vision of the human user and the void configured to allow the human user to use the LED facial mask while engaging in other activities; h) the light guide being between 0.3 and 0.7 millimeters in thickness, wherein the thickness eliminates the need for mechanical hot bending during manufacturing; i) the headpiece being a hollow headpiece; j) the emitter being contained within the hallow headpiece; k) the hollow headpiece having a universal serial bus (USB) charge port; l) the emitter being connected to the USB charge port through an electronic connector; m) the emitter configured to emit a red monochromatic light, a yellow monochromatic light, or a blue monochromatic light, wherein the emitter can emit the red monochromatic light the yellow monochromatic light, or the blue monochromatic light individually or the emitter can emit a combination of two or more of the red monochromatic light, the yellow monochromatic light, or the blue monochromatic light simultaneously; n) the emitter being a flexible printed circuit light emitting diode (LED) light bar; o) the light guide being made of a transparent material; p) the electronic connector being a flat printed circuit (FPC) connector; q) the emitter configured to emit the yellow monochromatic light or the blue monochromatic light either singularly or in combination at a wavelength between 470 nanometers to 630 nanometers and the red monochromatic light either singularly or in combination at a wavelength between 470 nanometers to 660 nanometers; r) at least one light channel being located on the light guide, wherein the at least one light channel corresponds to a positioning point on the hollow headpiece; and s) the USB charge port being located on a distal end of a left side or a right side of the hollow headpiece.

3. An LED facial mask comprising:
a) the LED facial mask configured to go around a head of a human user,
b) the LED facial mask having a retainer, a headpiece, and a light guide braced between the retainer and the headpiece;
c) a nosepiece, operably affixed to the LED facial mask, which is configured to rest on a nose of the human user, wherein the nosepiece is a Y-shaped nosepiece;
d) an emitter which emits a visible light radiation, the emitter comprising a plurality of light-emitting diodes, the emitter operably affixed to the LED facial mask;
e) the light guide operably affixed to the LED facial mask, wherein the visible light radiation is emitted by the emitter onto the light guide and a body of the light guide is configured to transmit the visible light radiation onto a face of the human user;
f) a dot-dash line, wherein the dot-dash line comprises at least two dots, each dot comprising a penetrating void in the light guide and the dot-dash line configured to cause a portion of the visible light radiation emitted by the emitter to be emitted onto the face of the human user;
g) a void in the dot-dash line, the void configured to be within a field of vision of the human user and the void configured to allow the human user to use the LED facial mask while engaging in other activities;
h) the dot-dash line having a density of dots, the density of dots increasing when the dots are closer together and the density of dots decreasing when the dots are further apart, the emitter being in a fixed position and the dot-dash line being placed, wherein there is an increase in the density of dots as the distance from the emitter becomes greater over a surface of the light guide:
i) the headpiece being a hollow headpiece;
j) the emitter being contained within the hollow headpiece;
k) a timing switch, the timing switch being configured to be activated by the human user and causing the emitter to emit the visible light radiation for a limited period of time;
l) the hollow headpiece having a universal serial bus (USB) charge port;
m) the emitter being connected to the USB charge port through an electronic connector;
n) the emitter configured to emit a red monochromatic light, a yellow monochromatic light, or a blue monochromatic light, wherein the emitter can emit the red monochromatic light, the yellow monochromatic light, or the blue monochromatic light individually or the emitter can emit combination of two or more of the red monochromatic light, the yellow monochromatic light, or the blue monochromatic light simultaneously;
o) the emitter being a flexible printed circuit light emitting diode (LED) light bar;
p) the light guide being made of a transparent material;
q) the electronic connector being a flat printed circuit (FPC) connector;
r) the emitter configured to emit the yellow monochromatic light or the blue monochromatic light either singularly or in combination at a wavelength between 470 nanometers to 630 nanometers and the red monochromatic light either singularly or in combination at a wavelength between 470 nanometers to 660 nanometers;
s) the hollow headpiece and the retainer being secured to each other with at least one buckle;
t) the retainer having a left side and a right side and the nosepiece being secured at a position that is in the middle as measured from a distal end of both the left side and the right side;
u) at least one light channel being located on the light guide, wherein the at least one light channel corresponds to a positioning point on the hollow headpiece; and
v) the USB charge port being located on the distal end of a left side or a right side of the hollow headpiece.

* * * * *